(12) United States Patent
Iijima et al.

(10) Patent No.: US 6,720,010 B2
(45) Date of Patent: Apr. 13, 2004

(54) COMPOSITION HAVING ANTIHEPATITIC ACTIVITY

(75) Inventors: Hideshi Iijima, Akishima (JP); Aizo Iijima, Kitasaitama-gun (JP)

(73) Assignee: Iijima Corporation, Akishima (JP)

( * ) Notice: Subject to any disclaimer, the term of this patent is extended or adjusted under 35 U.S.C. 154(b) by 0 days.

(21) Appl. No.: 10/265,224

(22) Filed: Oct. 7, 2002

(65) Prior Publication Data

US 2003/0113418 A1 Jun. 19, 2003

(30) Foreign Application Priority Data

Nov. 16, 2001 (JP) ........................................ 2001-350950

(51) Int. Cl.⁷ ........................ A61K 35/54; A61K 35/80; A61K 35/78; G01N 33/02
(52) U.S. Cl. .................. 424/581; 424/195.17; 424/725; 426/231
(58) Field of Search ........................... 424/581, 195.17, 424/725; 426/231

(56) References Cited

U.S. PATENT DOCUMENTS

| | | |
|---|---|---|
| 3,607,304 A | 9/1971 | Levin |
| 4,902,509 A | 2/1990 | Turk et al. |

FOREIGN PATENT DOCUMENTS

WO   WO 01/91777   12/2001

OTHER PUBLICATIONS

A. Verdoliva, et al., Journal of Chromatography, vol. 749, No. 2, pp. 233–242, "Affinity Purification of Immunoglobulins From Chicken Egg Yolk Using a New Synthetic Ligand", 2000.

*Primary Examiner*—Christopher R. Tate
*Assistant Examiner*—Randall Winston
(74) *Attorney, Agent, or Firm*—Oblon, Spivak, McClelland, Maier & Neustadt, P.C.

(57) ABSTRACT

To conduct a search for natural drugs and their formulae derived from natural substances that hardly cause side effects and drug tolerance, based on quite a new idea having departed from conventional drugs such as Chinese galenicals, Chinese medicine formulae, etc. and to develop a composition that has an antihepatitic activity. A composition having an antihepatitic activity is provided, which comprises a dry product of defatted whole egg of eggs of a fowl bred by feeding a feed having blended therein an additive comprising a dry product of *Angelica keiskei*, a dry product of brown algae, and optionally a dry product of *Theaceae Camellia*. The composition may contain a dry product of *Angelica keiskei* and optionally a dry product of *Theaceae Camellia*. The compositions have antihepatitic activity and are derived from natural substances.

27 Claims, No Drawings

COMPOSITION HAVING ANTIHEPATITIC ACTIVITY

FIELD OF THE INVENTION

The present invention relates to compositions having antihepatitic activity containing components derived from natural substances, and more particularly to compositions having antihepatitic activity containing dry product of defatted whole egg of eggs of a fowl bred by feeding a feed containing dry products of certain plants.

BACKGROUND OF THE INVENTION

In Japan, chronic hepatitis afflicts a huge number of persons, a majority of which is occupied by hepatitis B virus (HBV) and hepatitis C virus (HCV) carriers. Chronic hepatitis is a disease very difficult to cure. It is highly possible that after a long progress it proceeds into cirrhosis and further into hepatoma and there is no decisive specific for curing it. Methods for curing the disease currently focus on interferon (IFN) treatment contemplated to control or disinfect viruses.

However, IFN treatment has its limit and there is no other decisive therapy, so that the therapy of chronic hepatitis takes a long period of time anyhow. Accordingly, an auxiliary treatment in which glycyrrhizin formulations or Chinese galenicals such as malgranda bu-supo is used in combination has been used widely as a means for inhibiting the progress of the disease and improving the liver function injury. In particular, malgranda bu-supo, one of Chinese galenicals, causes side effects to a lesser extent than other drugs do and is relatively high in therapeutic index in respect of inhibition of inflammation. Therefore, it has come to attention.

Recently, however, the very malgranda bu-supo has come to fail to give satisfaction since its use in combination with an IFN formulation, which is the first selected drug for chronic hepatitis C, has frequently caused a side effect called interstitial pneumonia and such combined use has become a contradiction.

In any rate, under the present circumstances where no potent radical cure other than IFN treatment is present, there is little alternative therapy that supplements it. Thus, the patients suffering from chronic hepatitis desire the appearance of a novel drug for the therapy of hepatitis, which can be used daily and continuously for a long period of time with peace in mind.

Under the circumstances, challenges have been made on utilization of Chinese galenicals other than malgranda bu-supo or compositions derived from other natural substances as antihepatitic drugs. Actually, many such challenges have been described or reported in many patent publications, academic literature, and the like. There remains an ample possibility that further searches on natural substances will result in finding effective drug components.

In the case of intractable diseases such as chronic hepatitis whose therapy takes a long period of time, it is needless to say that the problems of side effects of a drug to be used and of drug tolerance in that the affected area of a patient resists the drug will become serious hindrances to the therapy.

However, it is considered that the conventional methods in which a drug component alone is isolated and purified or semi-synthesized from a particular natural substance as a therapeutic drug cannot solve the above-mentioned problems. So far as the organism (or living body) recognizes the drug as a foreign matter containing a cytotoxic factor, the problems of side effects and drug tolerance cannot be avoided to occur. Furthermore, other problems on drugs derived from natural substances include one that in many cases the component found with difficulty is poor as a resource, so that its industrial application is impossible.

SUMMARY OF THE INVENTION

Therefore, an object of the present invention is to conduct a search for natural drugs and their formulae derived from natural substances that hardly cause side effects and drug tolerance, based on quite a new idea having departed from conventional drugs such as Chinese galenicals, Chinese medicine formulae, etc. and to develop a composition that has an antihepatitic activity.

Accordingly, the inventors of the present invention have made extensive studies with a view to solving the above-described problems and as a result they have found that a dry product of defatted whole egg (hereinafter referred to as "defatted whole egg dry product") of eggs produced by a fowl bred by feeding a feed to which a dry product of *Angelica keiskei* ("Ashitaba", in Japanese) (hereinafter referred to as "*Angelica keiskei* dry product") and optionally a dry product of *Theaceae Camellia* ("Tsubaki", in Japanese) (hereinafter referred to as "*Theaceae Camellia* dry product") has antihepatitic activity. Also, the inventors of the present invention have found that a composition containing in addition to the above-mentioned defatted whole egg dry product, the *Angelica keiskei* dry product and optionally the *Theaceae Camellia* dry product has antihepatitic activity.

That is, the inventors of the present invention have found that the composition containing the above-mentioned defatted whole egg dry product has antihepatitic activity, i.e., an activity of preventing an increase in serum transaminase level associated with liver diseases and also that the composition containing the defatted whole egg dry product, the *Angelica keiskei* dry product and optionally the *Theaceae Camellia* dry product has excellent antihepatitic activity.

The present invention has been accomplished based on these findings.

According to a first aspect of the present invention, the present invention relates to a composition having an antihepatitic activity, characterized by comprising a dry product of defatted whole egg of eggs of a fowl bred by feeding a feed having blended therein an additive comprising a dry product of *Angelica keiskei*, a dry product of brown algae, and optionally a dry product of *Theaceae Camellia*.

According to a second aspect of the present invention, the present invention relates to a composition according to the first aspect of the invention, wherein the fowl is a member selected from the group consisting of hens, ducks and quails.

According to a third aspect of the present invention, the present invention relates to a composition having antihepatitic activity, characterized by comprising a dry product of defatted whole egg of the first aspect of the invention and a dry product of *Angelica keiskei*.

According to a fourth aspect of the present invention, the present invention relates to a composition having antihepatitic activity, characterized by comprising a dry product of defatted whole egg of the first aspect of the invention, a dry product of *Angelica keiskei* and a dry product of *Theaceae Camellia*.

According to the present invention, novel natural drugs derived from natural substances departing from conventional drugs Chinese galenicals, Chinese medicine formulae, etc. are provided. That is, compositions that contain components derived from natural substances as effective components and have antihepatitic activity are provided. In particular, the compositions of the present invention are excellent in specific antihepatitic effect to trouble in liver induced by drugs.

In addition, the compositions of the present invention are extremely weak in toxicity so that it is expected that they can be utilized not only in the therapy of hepatitis, etc. as drugs but also in preventing the above-mentioned diseases by adding them to various foods and taking them daily.

DETAILED DESCRIPTION OF THE INVENTION

As described above, the present invention relates to compositions having antihepatitic activity derived from familiar products that have never been used conventionally as raw materials, such as *Angelica keiskei* and *Theaceae Camellia*, which are natural substances, as well as a dry product of whole egg defatted from specific eggs produced by utilizing such natural substances as feeds.

Although it is unclear as to what compound contained in the components constituting the composition of the present invention is the main body that exhibits pharmacological activity, it is believed that a plurality of compounds contained therein act in combination with each other.

*Angelica keiskei* used as a raw material in the present invention is an umbelliferous perennial plant known to have strong authigenic ability and contain abundant nutritional components. It is authigenically distributed mainly in the southern coasts of Izu peninsula and Izu islands, Japan. However, recently it is also cultivated as a vegetable or the like in Japan.

Various portions, such as leaves, stems, and roots, of *Angelica keiskei* may be used, with leaves and stems being preferred. There has been no report on utilization of *Angelica keiskei* as a component of a drug having antihepatitic activity.

The *Angelica keiskei* dry product used in the present invention can be obtained, for example, by cutting *Angelica keiskei* to a suitable size (usually 10 to 15 mm square) after optionally washing the leaves and stems of *Angelica keiskei* with water, freezing the cut plant pieces, and then sublimating the iced water in vacuum to dry them. The dry product is used usually after it is processed into the form of powder in consideration of convenience. This is yellowish green (young leaf color) powder. Hereinafter, the *Angelica keiskei* dry product is referred to as "I-01B".

*Theaceae Camellia* is an evergreen tall tree that is authigenically distributed in Honshu, Shikoku, Kyushu, etc. districts in Japan and includes many kinds of variations for appreciation, etc. prepared by breeding. In the present invention, a wild type of *Camellia japonica* (Yabutsubaki) is preferable.

The portions of *Theaceae Camellia* to be used in the present invention include leaves, flowers, seeds, etc., with leaves being particularly preferable. Thus far no report has been made on utilization of leaves, etc. of *Theaceae Camellia* as components of drugs. In the present invention, the *Theaceae Camellia* dry product obtained by roasting, for example, leaves, etc. of *Theaceae Camellia* are used as the *Theaceae Camellia* dry product. As an example thereof, first, picked *Theaceae Camellia* leaves are dried. The drying is performed by heating them at 60 to 80° C. for 3 to 5 hours. Then, the dry product is cut to a suitable size (usually, about 5 mm square) and then roasted. The roasting is performed generally by using a hot iron plate drum type roasting apparatus at 100 to 150° C. for 10 to 30 minutes. For the same reason as in the case of the dry product of *Angelica keiskei*, usually powdered *Theaceae Camellia* is used. This is brown powder. Hereinafter, the *Theaceae Camellia* dry product is referred to as "I-01C".

The eggs produced by fowls to be used in the present invention are those eggs produced by fowls bred by feeding with a feed containing an additive comprising I-01B and a dry product of brown algae (hereinafter referred to as "brown algae dry product"), for example, dried tangle weed, as an auxiliary component, or a feed containing an additive comprising I-01B, I-01C and a brown algae dry product. Note that as basal feeds, those feeds commonly used in breeding fowls are used. For preparing feed additives, respective raw materials are blended in the following ratios: (1) I-01B:brown algae dry product=1–4:1–4 (by weight ratio), preferably 1:1 (by weight ratio), or (2) I-01B:I-01C:brown algae dry product=1–4:1–4:1–4 (by weight ratio), preferably 2:1:1 (by weight ratio).

The blending amounts of the additives to the feed are not particularly limited but in the case of the additive (1), the blending amount of the additive is 1 to 20% by weight, preferably 2 to 8% by weight while in the case of the additive (2), the blending amount of the additive is 1 to 20% by weight, preferably 2 to 8% by weight.

Fowls may be bred by a conventional method except that the special additives as described above are blended to the feed. The fowls include hens, ducks, quails, etc., with hens being preferable.

Eggs must be collected after at least 10 days' feeding on a feed having blended therein the above-mentioned additives. The reason thereof resides in that, generally, the period during which the components contained in the feed additive move over into eggs is considered to be about 3 days in the case of water-soluble components and about 3 weeks in the case of fat-soluble components. However, according to the finding by the inventors of the present invention, a conclusion has been obtained that it is desirable that egg collection is done after feeding the feed containing the above-mentioned additive to the fowls for at least 10 days.

Moreover, although details are unclear, the inventors of the present invention have found that proteins in the above-mentioned eggs are useful for the purpose of the present invention.

Accordingly, the whole egg obtained from eggs collected is defatted and dried to obtain a dry product. That is, liquid egg obtained by cracking eggs is sufficiently agitated to homogenize it and then frozen by a conventional method to obtain frozen whole egg, which then is dried. The drying is performed preferably by using a microwave drier under controlling the power and heating time of the microwave drier so that the temperature of the product does not exceed a range of 80 to 90° C. This can provide a whole egg dry product in the form of chips.

Then, the whole egg dry chips are defatted by extracting them by distillation with an alcohol such as methanol, ethanol, etc., as an extraction solvent, and thereafter, the defatted whole egg is recovered. Note that at the time of extraction, the solvent is heated to a temperature not higher than 60° C. and the extraction is completed within 1.5 hours, preferably in from 30 minutes to 1 hour. If necessary, this defatting treatment may be repeated several times.

By applying a hot air drying to the defatted whole egg, a whole egg dry product is obtained. Note that it is preferred that the hot air drying is performed by using a hot air fluidized bed type drier or the like. Since powder is desirable also in the case of whole egg dry product, usually powdered whole egg dry product is used. This can be obtained by pulverizing the whole egg dry product to a suitable size by using, for example, a pulverizer such as a hammer mill. The whole egg dry product thus obtained has a pale brown color. The defatted whole egg dry product derived from eggs obtained by breeding fowls with a feed having blended therein the additive (1) is referred to as "I-01A(1)", and the defatted whole egg dry product derived from eggs obtained by breeding the fowls with a feed having blended therein the additive (2) is referred to as "I-01A(2)".

The composition containing, as active components, I-01A, which is the above-mentioned defatted whole egg dry product, specifically I-01A(1) or I-01A(2), is the composition having antihepatitic activity according to the first aspect of the present invention.

On the other hand, the composition containing, as active components, I-01A, which is the above-mentioned defatted whole egg dry product, I-01B, which is the above-mentioned *Angelica keiskei* dry product, and optionally I-01C, which is the above-mentioned *Theaceae Camellia* dry product, is a composition having antihepatitic activity according to the third or fourth embodiment of the present invention.

The drug compositions of the present invention are very low in toxicity. For example, in a repetitive administration of mixed feed in which a composition containing I-01A and I-01B in combination is administered to rats for 2 weeks at a mixed ratio of 30%, no toxicity was observed.

In the case of other compositions containing other combinations, in mouse leukemia pharmacological experiments conducted by administration at a mixed ratio of 20 to 45%, there has been observed no change suggesting toxicity in general states such as body weight, feed taking amount, amount of exercise, etc. throughout the period of 10 days before transplantation of leukemia cells and survival period after the transplantation as compared to the non-administered control group. In addition, they exhibited significant anticancer effect of 200% or more in terms of life sustaining ratio.

Therefore, the drug compositions of the present invention are excellent in safety and can be used as food additives so that daily uptake thereof can prevent diseases.

The drug compositions of the present invention are administered mainly by an oral route. The form of the compositions is not particularly limited and they can be prepared into capsules, granules, tablets, etc. by, for example, a conventional preparation method.

The dosages and blending ratios of the respective components when the drug compositions of the present invention are used for humans are as follows. For example, in the case of the composition according to the first aspect of the invention, it is suitable to administer the composition such that I-01A is administered at a dosage of 0.2 to 20 g/day, preferably 1 to 5 g/day. In the case of the composition according to the third or fourth aspect of the invention containing a blend of I-01A and I-01B, it is suitable to administer the composition in a blending ratio of I-01A:I-01B =1–10:0.5–5, preferably 1–2:0.5–1, at a dosage of 0.2 to 20 g/day, preferably 1 to 5 g/day. Also, in the case of the composition having a formulation of I-01A, I-01B and I-01C, it is suitable to administer the composition in a blending ratio of I-01A:I-01B:I-01C=1–10:0.5–5:0.5–5, preferably 1–2:0.5–1:0.5–1 at a dosage of 0.2 to 20 g/day, preferably 1 to 5 g/day.

The blending ratios and dosages of the respective components described above are merely exemplary and since the components are not toxic, the blending ratios and dosages are not particularly limited to the above-mentioned values and various preparations and formula patterns of dosage in consideration of conditions such as site of disease, progress of disease, state of disease, sex, age, etc. as appropriate are applicable.

Furthermore, also when the drug compositions of the present invention are used as food additives, there is no fear of any toxicity or side effects, so that the addition amounts to foods, etc. may be determined in consideration of the above-mentioned preparations and formula patterns of dosage, etc.

EXAMPLES

Hereinafter, the present invention will be described in detail by examples. However, the present invention should not be considered as being limited thereto.

Production Example 1
Production of Ashitaba Dry Product
(1) Leaves and stems of *Angelica keiskei* (Ashitaba) were cut from cultivation field of *Angelica keiskei* to obtain 1,960 kg of a raw material. The length of the obtained stems was adjusted to 70 to 80 cm. Then, the raw material was washed with tap water. The component analysis of (raw) leaves of *Angelica keiskei* gave results as shown in Table 1.

The washed raw material was cut to about 10 to 15 mm square with a cutter.
(2) The cut raw material was placed on a tray and preliminarily frozen. Furthermore, after freezing the cut raw material in a freeze-drier, the freeze-drier was evacuated to sublimate the frozen water.

The obtained freeze-dried product was pulverized in a pulverizer to a size of about 100 meshes. Thus, 238.5 kg of *Angelica keiskei* dry product powder I-01B was obtained.

TABLE 1

| General Components Composition | |
|---|---|
| Item | Content* |
| Water | 88.6 g |
| Protein | 3.3 g |
| Lipids | 0.1 g |
| Ash | 1.3 g |
| Carbohydrates (sugars) | 5.2 g |
| Carbohydrates (fibers) | 1.5 g |
| Energy | 33 kcal |
| Sodium | 60 mg |
| Potassium | 540 mg |
| Substantial amount of salt | 0.2 g |

*Quoted from "Fourth Edition, Japan Standard Tables of Food Composition (1982)"

Production Example 2
Production of Camellia Dry Product
(1) Raw leaves of *Camellia japonica* (Yabutsubaki, wild type) were picked to obtain 476 kg of a raw material. The raw material was washed with tap water. Then, the raw material was heated at 70° C. for 5 hours to obtain a dry product, which then was roasted on a hot iron plate at 135° C. for 15 minutes to obtain a roasted dry product.
(2) The above-mentioned roasted dry product was pulverized by a pulverizer to a size of about 30 meshes to obtain 116.7 kg of *Theaceae Camellia* dry product powder I-01C.

The component analysis of the *Theaceae Camellia* dry product powder I-01C was performed. That is, general components composition, amino acid composition and fatty acid composition in 100 g of edible portion were examined. The results obtained are shown in Tables 2, 3, and 4, respectively.

TABLE 2

General Components Composition

| Item | Content |
| --- | --- |
| Water | 5.4 g |
| Protein | 9.0 g |
| Lipids | 3.9 g |
| Ash | 5.9 g |
| Carbohydrates | 75.6 g |
| Energy | 374 kcal |
| Sodium | 129 mg |
| Substantial amount of salt | 0.3 g |
| Tannic acid | 5200 mg |

TABLE 3

Amino Acid Composition

| Item | Content (mg) |
| --- | --- |
| Arginine | 356 |
| Lysine | 414 |
| Histidine | 163 |
| Phenylalanine | 399 |
| Tyrosine | 226 |
| Leucine | 668 |
| Isoleucine | 298 |
| Methionine | 48 |
| Valine | 384 |
| Alanine | 456 |
| Glycine | 470 |
| Proline | 392 |
| Glutamic acid | 858 |
| Serine | 387 |
| Threonine | 357 |
| Aspartic acid | 626 |
| Cystine | 7 |
| Hydroxyproline | 94 |
| γ-aminobutric acid | 52 |

TABLE 4

Fatty Acid Composition

| Item | Content (g) |
| --- | --- |
| Palmitic acid | 0.30 |
| Palmitoleic acid | 0.06 |
| Stearic acid | 0.03 |
| Oleic acid | 0.10 |
| Linoleic acid | 0.08 |
| Linolenic acid | 0.20 |

Production Example 3
Production of Egg (Part 1)
(1) Preparation of Feed Additive The *Angelica keiskei* dry product I-01B obtained in Production Example 1 and commercially available cut tangle weed (dry product) were mixed in a weight ratio of 1:1 to pepare a feed additive.
(2) Preparation of Feed To a basal feed (trade name: Kumiai Blended Feed for Adult Chicken SELECT, produced by Asahi Industries Co., Ltd.; composition, 61% of grains, 20% of plant oil cakes, 5% of animal-derived feed, 4% of chaff and bran, 10% of miscellaneous) was blended 2% by weight of the feed additive obtained as described in (1) above to prepare a feed.

(3) Feeding and Egg Collection

A thousand (1,000) egg-laying hens which were all 300 days old were given the feed as described in (2) above and allowed to freely take it. Egg-laying ratio was good and no difference in egg-laying ratio from that of normal egg-laying hens fed under the same conditions was observed. After 10 days from the start of feeding, eggs were continuously collected for 23 days to obtain 1,200 kg of eggs.

(4) Component analysis of the egg obtained as described in (3) above was performed. That is, the general components composition and amino acid composition in 100 g of edible portion were examined. The results obtained are shown in Tables 5 and 6, respectively.

TABLE 5

General Components Composition

| Item | Egg of the present invention | Control egg* |
| --- | --- | --- |
| Water | 74.9 g | 74.7 g |
| Protein | 12.8 g | 12.3 g |
| Lipids | 10.1 g | 11.2 g |
| Ash | 1.0 g | 0.9 g |
| Carbohydrates | 1.2 g | 0.9 g |
| Energy | 147 kcal | 162 kcal |
| Sodium | 147 mg | 130 mg |
| Cholesterol | 471 mg | 470 mg |
| Iodine | 0.4 mg | (0.02 mg)** |

*Quoted from "Fourth Edition, Japan Standard Tables of Food Composition (1982)"
**Calculated value

TABLE 6

Amino acid Composition (content in grams)

| Item | Egg of the present invention | Control egg* |
| --- | --- | --- |
| Arginine | 0.84 | 0.78 |
| Lysine | 0.97 | 0.89 |
| Histidine | 0.34 | 0.31 |
| Phenylalanine | 0.72 | 0.64 |
| Tyrosine | 0.58 | 0.50 |
| Leucine | 1.15 | 1.10 |
| Isoleucine | 0.69 | 0.68 |
| Methionine | 0.46 | 0.40 |
| Valine | 0.86 | 0.83 |
| Alanine | 0.74 | 0.70 |
| Glycine | 0.44 | 0.41 |
| Proline | 0.49 | 0.47 |
| Glutamic acid | 1.71 | 1.60 |
| Serine | 0.99 | 0.84 |
| Threonine | 0.63 | 0.57 |
| Aspartic acid | 1.34 | 1.30 |
| Tryptophan | 0.19 | 0.19 |
| Cystine | 0.36 | 0.32 |

*Quoted from "Revised Japan Standard Tables of Food Composition (1986)"

Production Example 4
Production of Egg (Part 2)
(1) Preparation of Feed Additive The *Angelica keiskei* dry product I-01B obtained in Production Example 1, the *Theaceae Camellia* dry product I-01C obtained in Production Example 2, and commercially available cut tangle weed (dry product) were mixed in a weight ratio of 2:1:1 to obtain a feed additive.
(2) Preparation of Feed To a basal feed (trade name: Kumiai Blended Feed for Adult Chicken SELECT, produced by Asahi Industries Co., Ltd.; composition, 61% of grains, 20% of plant oil cake, 5% of animal-derived feed, 4% of chaff and bran, 10% of miscellaneous) was blended 8% by weight of the feed additive obtained as described in (1) above to prepare a feed.

(3) Feeding and Egg Collection

Seven hundred (700) egg-laying hens which were all 180 days old were given the feed as described in (2) above and allowed to freely take it. Egg-laying ratio was good and no difference in egg-laying ratio from that of normal egg-laying hens fed under the same conditions was observed. After 10 days from the start of feeding, eggs were continuously collected for 35 days to obtain 1,150 kg of eggs.

(4) Component analysis of the egg obtained as described in (3) above was performed. That is, the general components composition and amino acid composition in 100 g of edible portion were examined. The results obtained are shown in Tables 7 and 8, respectively.

TABLE 7

General Components Composition

| Item | Egg of the present invention | Control Egg * |
|---|---|---|
| Water | 75.6 g | 74.7 g |
| Protein | 13.2 g | 12.3 g |
| Lipids | 8.6 g | 11.2 g |
| Ash | 0.8 g | 0.9 g |
| Carbohydrates | 1.8 g | 0.9 g |
| Energy | 137 kcal | 162 kcal |
| Sodium | 132 mg | 130 mg |
| Cholesterol | 412 mg | 470 mg |
| Iodine | 0.18 mg | (0.02 mg)** |

* Quoted from "Fourth Edition, Japan Standard Tables of Food Composition (1982)"
**Calculated value

TABLE 8

Amino Acid Composition (content in grams)

| Item | Egg of the present invention | Control egg* |
|---|---|---|
| Arginine | 0.86 | 0.78 |
| Lysine | 0.97 | 0.89 |
| Histidine | 0.30 | 0.31 |
| Phenylalanine | 0.73 | 0.64 |
| Tyrosine | 0.50 | 0.50 |
| Leucine | 1.14 | 1.10 |
| Isoleucine | 0.56 | 0.68 |
| Methionine | 0.43 | 0.40 |
| Valine | 0.70 | 0.83 |
| Alanine | 0.78 | 0.70 |
| Glycine | 0.49 | 0.41 |
| Proline | 0.50 | 0.47 |
| Glutamic acid | 1.78 | 1.60 |
| Serine | 0.96 | 0.84 |
| Threonine | 0.57 | 0.57 |
| Aspartic acid | 0.99 | 1.30 |
| Tryptophan | 0.08 | 0.19 |
| Cystine | 0.26 | 0.32 |

*Quoted from "Revised Japan Standard Tables of Food Composition (1986)"

Production Example 5
Production of Defatted Whole Egg Dry Product (Part 1)

(1) Freezing of Whole Egg 1,160 kg of whole egg obtained in Production Example 3 was cracked, and thus obtained liquid whole egg was sufficiently agitated and then frozen to obtain 938.9 kg of frozen whole egg.

(2) Drying Treatment

The frozen whole egg as described in (1) above was dried by microwave to obtain dry whole egg chips. When performing the drying, the temperature of the product was controlled so as to be kept at no higher than 90° C.

(3) Defatting Treatment

The dry whole egg chips as described in (2) above were refluxed with ethanol heated at 60° C. to extract lipids. The extraction time for lipids was set to 1 hour per time and the defatting was performed 2 times. Thereafter, the solvent and lipids were recovered by distillation to obtain the objective defatted extract.

(4) Drying Treatment

The defatted extract obtained as described in (3) above was subjected to hot air drying with a hot air fluidized bed type drier to obtain a defatted whole egg dry product.

(5) Pulverizing Treatment

The defatted whole egg dry product obtained as described in (4) above was pulverized to a size of about 100 meshes by using a hammer mill to obtain 111.3 kg of the objective defatted whole egg dry product powder I-01A(1).

(6) Component analysis of the defatted whole egg dry product powder I-01A(1) obtained as described in (5) above was performed. That is, the general components composition and amino acid composition in 100 g of edible portion were examined. The results obtained are shown in Tables 9 and 10, respectively.

TABLE 9

General Components Composition

| Item | I-01A(1) | Control dried whole egg* |
|---|---|---|
| Water | 5.4 g | 3.2 g |
| Protein | 86.9 g | 47.2 g |
| Lipids | 0.8 g | 41.7 g |
| Ash | 3.6 g | 3.8 g |
| Carbohydrates | 3.3 g | 4.1 g |
| Energy | 366 kcal | 611 kcal |
| Sodium | 569 mg | 500 mg |
| Substantial amount of salt | 1.4 g | 1.3 g |

*Quoted from "Fourth Edition, Japan Standard Tables of Food Composition (1982)"

TABLE 10

Amino Acid Composition (content in milligrams)

| Item | I-01A(1) |
|---|---|
| Arginine | 4774 |
| Lysine | 4955 |
| Histidine | 1808 |
| Phenylalanine | 4086 |
| Tyrosine | 2895 |
| Leucine | 6762 |
| Isoleucine | 3585 |
| Methionine | 2499 |
| Valine | 4410 |
| Alanine | 4626 |
| Glycine | 2832 |
| Proline | 2903 |
| Glutamic acid | 11172 |
| Serine | 6422 |
| Threonine | 3797 |
| Aspartic acid | 8416 |
| Tryptophan | 51 |
| Cystine | 1549 |

Production Example 6
Production of Defatted Whole Egg Dry Product (Part 2)

(1) Freezing of Whole Egg 1,090 kg of whole egg obtained in Production Example 4 was cracked, and thus obtained liquid whole egg was sufficiently agitated and then frozen to obtain 890 kg of frozen whole egg.

(2) Drying Treatment

The frozen whole egg as described in (1) above was dried by microwave to obtain dry whole egg chips. When performing the drying, the temperature of the product was controlled so as to be kept at no higher than 90° C.

(3) Defatting Treatment

The dry whole egg chips as described in (2) above were refluxed with ethanol heated at 60° C. to extract lipids. The extraction time for lipids was set to 1 hour per time and the defatting was performed 2 times. Thereafter, the solvent and lipids were recovered by distillation to obtain the objective defatted extract.

(4) Drying Treatment

The defatted extract obtained as described in (3) above was subjected to hot air drying with a hot air fluidized bed type drier to obtain a defatted whole egg dry product.

(5) Pulverizing Treatment

The defatted whole egg dry product obtained as described in (4) above was pulverized to a size of about 100 meshes by using a hammer mill to obtain 104.38 kg of the objective defatted whole egg dry product powder I-01A(2).

(6) Component analysis of the defatted whole egg dry product powder I-01A(2) obtained as described in (5) above was performed. That is, the general components composition and amino acid composition in 100 g of edible portion were examined. The results obtained are shown in Tables 11 and 12, respectively.

TABLE 11

General Components Composition

| Item | I-01A(2) | Control dried whole egg* |
|---|---|---|
| Water | 5.3 g | 3.2 g |
| Protein | 82.7 g | 47.2 g |
| Lipids | 3.5 g | 41.7 g |
| Ash | 3.8 g | 3.8 g |
| Carbohydrates | 4.7 g | 4.1 g |
| Energy | 381 kcal | 611 kcal |
| Sodium | 685 mg | 500 mg |
| Substantial amount of salt | 1.7 g | 1.3 g |

*Quoted from "Fourth Edition, Japan Standard Tables of Food Composition (1982)"

TABLE 12

Amino Acid Composition (content in milligrams)

| Item | I-01A(2) |
|---|---|
| Arginine | 4672 |
| Lysine | 4813 |
| Histidine | 1868 |
| Phenylalanine | 3981 |
| Tyrosine | 2670 |
| Leucine | 6571 |
| Isoleucine | 3512 |
| Methionine | 2295 |
| Valine | 4280 |
| Alanine | 4536 |
| Glycine | 2773 |
| Proline | 2811 |
| Glutamic acid | 10860 |
| Serine | 6215 |
| Threonine | 3699 |
| Aspartic acid | 8218 |
| Tryptophan | 63 |
| Cystine | 1541 |

Example 1

Using the defatted whole egg dry product powder I-01A (1) produced in Production Example 5 above, the in vivo inhibitory effect on carbon tetrachloride-induced liver injury was examined.

Carbon tetrachloride was formulated as a 50% olive oil solution and the solution was intraperitoneally administered to rats at a dosage of 1.5 ml/kg body weight to prepare liver injured model rats.

As the test substance, suspensions of the defatted whole egg dry product powder I-01A(1) in 0.5% carboxymethyl-cellulose sodium (produced by Kanto Kagaku Kogyo Co., Ltd.) solutions in a concentration of 0.8 mg/ml or 80 mg/ml were prepared. Tests were performed by forcibly administering the suspensions to the laboratory animals (SD rats (Cri:IGS) of 6 weeks old) by an oral route.

The tests were performed on the laboratory animals divided into groups (8 animals per group) depending on the dosage of the test substance and the number of times of administration. That is, the number of times of administration for two groups on which the dosages were 16 mg/kg and 1,600 mg/kg, respectively, was set to three and separately, the number of times of administration for one group on which the dosage was 1,600 mg/kg was set to 1.

For the test lot with the number of times of administration being 3, administrations were performed in total three times consisting of two times being 2 days before the administration of carbon tetrachloride and one time being 1 hour after the administration of carbon tetrachloride. For the test lot with the number of times of administration being one, the administration was performed only once 1 hour after the administration of carbon tetrachloride. One group without administration of the test substance was served as a control group.

After 24 hours from the administration of the test substance, blood was extracted from the abdominal aorta and then centrifuged at 3,000 rpm for 15 minutes to obtain serum. The serum was measured on GOT and GPT by using an Autoanalyzer (produced by Toshiba Medical Systems Co., Ltd.) to examine the inhibitory effect on liver injury. The results obtained are shown in Table 13.

TABLE 13

Results of Measurement of GOT and GPT

| Lot | | GOT(IU/L) | GPT(IU/L) |
|---|---|---|---|
| Control group | | 2692.6 | 851.6 |
| I-01A(1)- | 16 mg/kg × 3 times | 1664.0 | 521.5 |
| administered | 1600 mg/kg × 3 times | 2100.9 | 648.6 |
| group | 1600 mg/kg × 1 time | 1480.4 | 523.5 |

Example 2

Using a 11:4 (weight ratio) mixture of the defatted whole egg dry product powder I-01A(1) produced in Production Example 5 above and the *Angelica keiskei* dry product I-01B produced in Production Example 1 above, the in vivo inhibitory effect on carbon tetrachloride-induced liver injury was examined.

Similarly to Example 1, carbon tetrachloride was formulated as a 10% olive oil solution, and the solution was intraperitoneally administered to mice at a dosage of 5 ml/kg body weight on day 6 of the administration of the test substance to prepare liver injured model mice.

As the test substance, a composition containing a mixture of the defatted whole egg dry product powder, I-01A(1), and the *Angelica keiskei* dry product, I-01B, (I-01A(1): I-01B= 11:4 (ratio by weight) was blended in a powdered basal feed (trade name: CF2, produced by CLEA Japan, Inc.) at a mixing ratio of 0.5% or 5%. The tests were performed by allowing laboratory animals (CDF$_1$ mice (Cri:CDF$_1$) of 6 weeks old) to freely take this composition via oral administration. The number of days of administration was set to seven days.

The tests were performed on the laboratory animals divided into two groups, one administered with the feed with the mixing ratio of the test substance being 0.5% and the other administered with the feed with the mixing ratio of the test substance being 5% (8 animals per group). Also, one group administered with no test substance was used as a control group.

After one day from the administration of carbon tetrachloride, blood was extracted from the postcava of the mice and then centrifuged at 3,000 rpm for 15 minutes to obtain serum. The serum was measured on GOT and GPT by using an Autoanalyzer (produced by Toshiba Medical Systems Co., Ltd.) to examine the inhibitory effect on liver injury. The results obtained are shown in Table 14.

TABLE 14

Results of Measurement of GOT and GPT

| Lot | | GOT(IU/L) | GPT(IU/L) |
| --- | --- | --- | --- |
| Control group | | 4931.0 | 13742.0 |
| I-01A(1):I-01B administered group | 0.5%-Feed mixing ratio | 4831.0 | 13521.9 |
| | 5%-Feed mixing ratio | 2198.9 | 7015.4 |

Example 3

Using a composition I-01A(2): I-01B: I-01C prepared by adding the *Theaceae Camellia* dry product, I-01C, produced in Production Example 2 to a mixture of the defatted whole egg dry product powder, I-01A(2), produced in Production Example 6 above and the *Angelica keiskei* dry product, I-01B, produced in Production Example 1 above, and I-01A (2) alone as test substances, the in vivo inhibitory effect on carbon tetrachloride-induced liver injury was examined.

That is, a mixed feed prepared by blending a composition containing I-01A(2), I-01B, and I-01C in a weight ratio of 65:35:5 or I-01A(2) on its own in a basal feed was orally administered to laboratory animals (Cri:CD(SD)IGS rats, 6 weeks old) by allowing them to freely take it. Note that, as the basal feed was used a powdered feed (trade name: CRF, produced by Oriental Yeast Industry Co., Ltd) each with a mixing ratio of 5%.

The groups administered with the test substances were two groups described above and one group administered with no test substance was used as a control group. The tests were performed with the number of animals in each group being 8.

Carbon tetrachloride was formulated as a 50% olive oil solution, and the solution was administered to the dorsal hypodermis of rats at a dosage of 2.5 ml/kg body weight on day 7 of the administration of the test substance to prepare liver injured model rats.

After 24 hours from the administration of carbon tetrachloride, blood was extracted from the cervical vein and then centrifuged at 3,000 rpm for 15 minutes to obtain serum. The serum was measured on GOT and GPT by using an Autoanalyzer (7150 auto-analyzing apparatus, produced by Hitachi, Ltd.) to examine the inhibitory effect on liver injury. The results obtained are shown in Table 15.

TABLE 15

Results of Measurement of GOT and GPT

| Lot | | GOT(IU/L) | GPT(IU/L) |
| --- | --- | --- | --- |
| Control group | | 295.6 | 72.5 |
| I-01A(2)-administered group | 5%-Feed mixing ratio | 203.4 | 53.9 |
| I-01A(2):I-01B:I-01C-administered group | 5%-Feed mixing ratio | 146.3 | 42.2 |

Example 4

Tests were carried out using the same composition and in the same manner as in Example 3 except that instead of the composition containing I-01A(2):I-01B:I-01C in a weight ratio of 65:35:5, a composition containing I-01A(1):I-01B:I-01C in a weight ratio of 65:35:5 was used. Results showed antihepatitic activity as seen in Example 3.

What is claimed is:

1. A composition having an antihepatitic activity comprising a dry product of defatted whole egg obtained from a hen which has been fed a feed having blended therein an additive comprising a dry product of *Angelica keiskei*, and a dry product of brown algae.

2. The composition having antihepatitic activity according to claim 1, further comprising a dry product of *Angelica keiskei*.

3. The composition having antihepatitic activity according to claim 1, further comprising a dry product of *Angelica keiskei* and a dry product of Theaceae.

4. The composition of claim 1, wherein the feed further comprises a dry product of Theaceae.

5. The composition of claim 4, which further comprises a dry product of *Angelica keiskei*.

6. The composition of claim 4, which further comprises a dry product of *Angelica keiskei* and a dry product of Theaceae.

7. The composition of claim 3, wherein the Theaceae is *Camellia japonica*.

8. The composition of claim 4, wherein the Theaceae is *Camellia japonica*.

9. The composition of claim 6, wherein the Theaceae is *Camellia japonica*.

10. The composition of claim 1, wherein the weight ratio of the dry product of *Angelica keiskei* to the dry product of brown algae in the feed is from 1 to 4 parts of the dry product of *Angelica keiskei* to from 1 to 4 parts of the dry product of brown algae.

11. The composition of claim 8, wherein the weight ratio of the dry product of *Angelica keiskei* to the dry product of brown algae in the feed is 1 to 1.

12. The composition of claim 4, wherein the weight ratio of the dry product of *Angelica keiskei*, the dry product of brown algae, and the dry product of Theaceae in the feed is from 1 to 4 parts of the dry product of *Angelica keiskei*, from 1 to 4 parts of the dry product of brown algae, and from 1 to 4 parts of the dry product of Theaceae.

13. The composition of claim 4, wherein the weight ratio of the dry product of *Angelica keiskei*, the dry product of brown algae, and the dry product of Theaceae in the feed is 2 parts of the dry product of *Angelica keiskei*, 1 part of the dry product of brown algae, and 1 part of the dry product of Theaceae.

14. A method of making the composition of claim 1, comprising feeding a hen a feed comprising a dry product of *Angelica keiskei*, and a dry product of brown algae;

defatting a whole egg obtained from the hen; and drying the defatted egg.

15. A method of making the composition of claim 2, comprising feeding a hen a feed comprising a dry product of *Angelica keiskei*, and a dry product of brown algae;

defatting a whole egg obtained from the hen;

drying the defatted egg; and adding a dry product of *Angelica keiskei* to the dried defatted egg.

16. A method of making the composition of claim 3, comprising feeding a hen a feed comprising a dry product of *Angelica keiskei*, and a dry product of brown algae;

defatting a whole egg obtained from the hen;

drying the defatted egg; and adding a dry product of *Angelica keiskei* and a dry product of Theaceae to the dried defatted egg.

17. A method of making the composition of claim 4, comprising feeding a hen a feed comprising a dry product of *Angelica keiskei*, a dry product of brown algae, and a dry product of Theaceae;

defatting a whole egg obtained from the hen; and drying the defatted egg.

18. A method of making the composition of claim 5, comprising feeding a hen a feed comprising a dry product of *Angelica keiskei*, a dry product of brown algae, and a dry product of Theaceae;

defatting a whole egg obtained from the hen;

drying the defatted egg; and adding a dry product of *Angelica keiskei* to the dried defatted egg.

19. A method of making the composition of claim 6, comprising feeding a hen a feed comprising a dry product of *Angelica keiskei*, a dry product of brown algae, and a dry product of Theaceae;

defatting a whole egg obtained from the hen;

drying the defatted egg; and adding a dry product of *Angelica keiskei* and a dry product of Theaceae to the dried defatted egg.

20. A method of inhibiting liver injury comprising, administering to an individual in need thereof, the composition of claim 1 in an amount effective to inhibit liver injury therein.

21. A method of inhibiting liver injury comprising, administering to an individual in need thereof, the composition of claim 2 in an amount effective to inhibit liver injury therein.

22. A method of inhibiting liver injury comprising, administering to an individual in need thereof, the composition of claim 3 in an amount effective to inhibit liver injury therein.

23. A method of inhibiting liver injury comprising, administering to an individual in need thereof, the composition of claim 4 in an amount effective to inhibit liver injury therein.

24. A method of inhibiting liver injury comprising, administering to an individual in need thereof, the composition of claim 5 in an amount effective to inhibit liver injury therein.

25. A method of inhibiting liver injury comprising, administering to an individual in need thereof, the composition of claim 6 in an amount effective to inhibit liver injury therein.

26. A method of inhibiting liver injury comprising, administering to an individual in need thereof, the composition of claim 7 in an amount effective to inhibit liver injury therein.

27. A method of inhibiting liver injury comprising, administering to an individual in need thereof, the composition of claim 8 in an amount effective to inhibit liver injury therein.

* * * * *